United States Patent [19]

Strecker

[11] Patent Number: 5,628,784
[45] Date of Patent: May 13, 1997

[54] ENDOPROSTHESIS THAT CAN BE PERCUTANEOUSLY IMPLANTED IN THE BODY OF A PATIENT

[76] Inventor: Ernst P. Strecker, Vierordstrasse 7a, D-76228, Karlsruhe, Germany

[21] Appl. No.: 373,385

[22] Filed: Jan. 17, 1995

[30] Foreign Application Priority Data

Jan. 18, 1994 [DE] Germany .............. 44 01 227.6

[51] Int. Cl.⁶ .................................................... A61F 2/06
[52] U.S. Cl. ................ 623/1; 606/192; 606/194; 604/93; 604/96
[58] Field of Search ............... 623/1, 8; 604/96–104, 604/93; 606/191, 192, 194

[56] References Cited

U.S. PATENT DOCUMENTS

| | | | |
|---|---|---|---|
| 4,093,484 | 6/1978 | Harrison et al. | 604/96 X |
| 5,156,620 | 10/1992 | Pigott | 623/1 |
| 5,328,469 | 7/1994 | Coletti | 606/194 X |
| 5,360,443 | 11/1994 | Barone et al. | 606/194 X |
| 5,383,928 | 1/1995 | Scott et al. | 623/1 |

FOREIGN PATENT DOCUMENTS

| | | | |
|---|---|---|---|
| 2645750 | 10/1990 | France | 604/96 |
| 9100752 | 1/1991 | WIPO | 604/96 |
| 9220387 | 11/1992 | WIPO | 604/96 |

*Primary Examiner*—Mary Beth Jones
*Attorney, Agent, or Firm*—Max Fogiel

[57] ABSTRACT

An endoprosthesis that can be percutaneously implanted by means of a catheter in a patient's body, especially inside a blood vessel or other body cavity. The endoprosthesis is oblong and hollow. It can be expanded once properly implanted to fit the lumen of the vessel or cavity. It comprises a sleeve surrounding at least the outside of a skeleton. The sleeve and the skeleton are initially narrow enough to be implanted and expand once they have been implanted. Room is left between the outer surface of the sleeve of the implanted endoprosthesis and the inner surface of the vessel or cavity it is implanted in. Drugs or other substances can be delivered to the room through at least one length of flexible tubing communicating with the sleeve. The sleeve can have spacers projecting radially out of it. The sleeve can also be a hollow membrane with the flexible tubing communicating with it. The sleeve is wrapped around the skeleton, leaving wrinkles and folds.

31 Claims, 4 Drawing Sheets

FIG. 9

ENDOPROSTHESIS THAT CAN BE PERCUTANEOUSLY IMPLANTED IN THE BODY OF A PATIENT

BACKGROUND OF THE INVENTION

The present invention concerns an endoprosthesis that can be percutaneously implanted by means of a catheter in a patient's body, especially inside a blood vessel or other body cavity The endoprosthesis is oblong and hollow. It can be expanded, once properly implanted, to fit the lumen of the vessel or cavity.

Percutaneously implanted expanding endoprostheses are known. They are employed to open or dilate blood vessels. There are two major forms. One is compressed before implantation and allowed to expand resiliently to its original size once implanted. The other is slender and implanted unstressed and stretched with a balloon catheter once implanted.

The endoprosthesis described in European A 0 183 372 is accommodated on a balloon catheter and expanded and accordingly released into the blood vessel. This prosthesis constitutes a stent in the form of a flexible cylinder produced by knitting, crocheting, or other reticulating process from filaments of a tissue-compatible metal or plastic. The individual meshes comprise loosely connected loops. As the balloon inflates, the meshes deform plasticly and the prosthesis expands permanently.

Stents that expand automatically are known from European A 0 183 372 and U.S. Pat. No. 4,732,152. These prostheses are elastic. They are radially compressed before implantation and implanted in that state in the patient's body. Once the prosthesis is in place, the compression is eliminated and the device expands until it rests snug in the vessel or body cavity.

The endoprosthesis described in European A 0 183 372 is radially compressed before implantation and advanced in that state by a plunger through a catheter previously inserted into the vessel until the desired location is attained. Advancing the prosthesis through the catheter requires considerable force due to the considerable friction between the two devices.

The endoprosthesis described in U.S. Pat. No. 4,732,152 is woven and elastic. It is maintained compressed by a continuous double sleeve at the distal end. The sleeve is stripped from the compressed prosthesis like a sock from a foot. The concomitant friction can be decreased by liquid between the two halves of the sleeve. Although the decreased friction originally makes this approach look very elegant, it is very difficult to maneuver.

WO 93 121 985 A1 discloses a balloon catheter with an invariable lumen for angioplasties. The balloon is surrounded by another balloon containing a drug for treating the inner surface of the vessel or body cavity. The outer balloon is porous. The outside of the inner balloon demarcates in conjunction with the inner surface of the outer balloon an accommodation for the drug, which is delivered through a length of flexible tubing. How much of the drug penetrates the wall of the outer balloon extensively depends on the pressure inside the inner balloon. A lot of drug will be released, no matter how much is needed, when the inner balloon expands considerably in executing the angioplasty. The pressure of the emerging drug can actually damage the inner surface of the vessel when the outer balloon rests directly against it. It is impossible to control the dose independent of the expansion of the inner balloon.

SUMMARY OF THE INVENTION

The object of the present invention is accordingly an improved endoprosthesis of the aforesaid genus, which can be implanted with a catheter and expanded, that can be employed not only to establish communication with or between body cavities, remaining open after implantation, but for medication as well.

This object is attained in accordance with the present invention by providing the endoprosthesis with a tubular skeleton. At least the outside of the skeleton is surrounded by a sleeve. The skeleton and the sleeve expand together from a slender state that they are introduced in to a wider state that they are implanted in. At least one length of flexible tubing communicates with the sleeve. Drugs or other substances can be introduced through the tubing between the sleeve and the body cavity that accommodates it.

The sleeve around at least the outside of the skeleton of the implanted prosthesis in accordance with the present invention accordingly rests against the inner surface of the vessel or body cavity accommodating the prosthesis, and allows drugs or other substances between it and the surface. The precise doses of drug necessary for specific purposes can accordingly be administered to the adjacent inner surface of the vessel or body cavity without damage and be absorbed into it.

It is practical for the length of flexible tubing that delivers the drug or other substance to communicate with or with the vicinity of one end of the sleeve. The sleeve can be made of a permanently plasticly deformable material. The sleeve can alternatively be made of an elastically deformable material. The degree of elasticity can be prescribed.

The sleeve may be more voluminous than the skeleton and initially wrapped around it, leaving wrinkles that smooth out as the skeleton expands.

Although tests have demonstrated that the end of an endoprosthesis of this type will provide enough of a seal to prevent undesired migration of the drug or other substance delivered through the flexible tubing, a version wherein the ends of the expanded prosthesis are wider than its midsection has been demonstrated practical.

The endoprosthesis may have a skirt at each end that tapers out. Room is accordingly left between the rest of the prosthesis and the inner surface of the vessel or body cavity that drugs or other substances can be introduced into. Although this room will leak because the skirts do not rest tight against the inner surface, it will still accommodate a higher concentration of the substances. Furthermore, blood can flow through the room.

The skirts in one advanced version of the invention rest tight against the inner surface of the vessel or body cavity. One advantage of this version is that it prevents the circulating blood from rinsing the drug away. The skirts will rest even tighter against the inner surface of the vessel or cavity if they are resilient.

The skirts in the endoprosthesis may be larger. More area accordingly rests against the inner surface of the blood vessel or body cavity. The sealing action of the skirts is accordingly more effective.

The outside of the sleeve in another advanced version of the present invention has radially projecting spacers remote from its ends that keep the inner surface of the blood vessel or body cavity accommodating the endoprosthesis a prescribed distance off the sleeve. This approach dictates the capacity of the room between the sleeve and the inner surface.

An endoprosthesis may be removable in a practical way by initially extracting and removing the skeleton with the first auxiliary catheter. When the skeleton is knit out of metal filament, the tension will decrease its radius. The sleeve can now be extracted and removed with the second auxiliary catheter.

The outside of the sleeve may be coated, especially with liquid silicone, to prevent adhesion. This procedure ensures that the room remains open and that the ports that allow the drugs or other substances out of the sleeve will remain unobstructed.

When the sleeve is a hollow membrane, drugs or other substances can be deposited inside the blood vessel or body cavity being treated.

When the endoprosthesis skeletons are expandable, it has been demonstrated particularly practical for the sleeves to be expandable too. This feature is particularly important for treating aneurysms, local pathological dilation of a blood vessel.

Substances other than drugs can also be introduced into the room left to accommodate the drugs or other substances between the sleeve and the inner surface of the blood vessel or body cavity during implantation. Such substances can in particular be those that solidify into tunnel-like structures that support and adhere only to the inner surface of the vessel or cavity. This approach facilitates removing the endoprosthesis later. These substances can be blended with drugs and/or be biodegradable.

To allow the inner surface of the blood vessel or body cavity for example to be supplied with blood, such tunnels of solid material should have holes or pores all the way through their walls. This can be done very simply by providing the sleeve with spacers or corrugations that project radially outward.

The last-mentioned application of the endoprosthesis is particularly practical when the outside of the sleeve is coated with an antiadhesive to facilitate separating it from the solidified substances between the sleeve and the inner surface of the blood vessel or body cavity. A coating of silicone on the outer surface of the sleeve is practical and easy to apply.

It is also possible within the scope of the present invention, however, for the sleeve around the endoprosthesis skeleton to be a hollow membrane with at least one length of flexible tubing communicating with it to deliver drugs or other substances. When the membrane has holes or pores of a particular size, the drugs or other substances can be gradually emitted very effectively.

An endoprosthesis with a sleeve in the form of a hollow membrane of elastic material can on the other hand also be employed to pack aneurysms on blood vessels by carefully positioning an endoprosthesis mounted on a catheter along with the membrane in the vicinity of a bulge on a vessel and filling it by injecting a solidifying substance through the flexible drug-delivery tubing in order to stretch the membrane.

To allow the packing of even severe blood-vessel aneurysms, the hollow membrane in the advanced version of the present invention is more voluminous than the endoprosthesis skeleton, is at least partly secured to it, and is wrapped close around it leaving folds. When filler is injected into such a membrane through the aforesaid flexible drug-deliver tubing, the prosthesis will gradually unfold and penetrate into even major bulges and pockets in the wall of the vessel. It has been demonstrated particularly practical in this event for the membrane to be folded longitudinally in from the ends.

The flexible tubing that delivers drugs or other substances in another advanced version can be detached from the sleeve and detached or extracted from the hollow membrane once enough drug for adequate treatment or enough solidifying substance has been delivered. In this event, some means, an appropriate valve for example, of sealing off the membrane must again be provided.

The endoprosthesis may be a concrete embodiment of a sleeve outlet that can be closed again in this way.

If there are at least two lengths of flexible tubing for delivering drugs or other substances, components can be delivered to the room separately and allowed to combine and react on site into the desired substance, an epoxide, tissue adhesive, or ion-cured adhesive for example.

It has also been demonstrated practical for the sleeve around the endoprosthesis skeleton to be of biodegradable material so that it will dissolve inside the patient's body after a prescribed length of time.

A very wide range of skeletons can be employed with the endoprosthesis in accordance with the present invention. It has on the other hand been demonstrated particularly practical for the skeleton inside the sleeve to be a cylinder produced by knitting or other reticulating process. Netting of this type is be distinguished by a certain elasticity once open that will ensure it springs back into the expanded state after being subjected to external forces that deform it slightly. Such skeletons can either expand automatically or be expanded by balloon catheters. They can also be made of a material with memory and expand subject to the heat of the human body once implanted.

A drawstring that opens the netting can extend out of the proximal end of such an endoprosthesis skeleton. The netting can be opened with the drawstring and the skeleton easily extracted subsequent to implantation.

The drawstring can also be fastened to the flexible tubing that also extends out of the proximal end, so that the skeleton and sleeve can both be extracted at the same time. Axial tension applied to the prosthesis will reduce the cross-section of the skeleton, allowing easy extraction of the endoprosthesis by means of a catheter for example.

The sleeve in an advanced version can be extracted on the drawstring from the site of implantation once the netting has been opened.

It is practical for the endoprosthesis skeleton to be made out of insulated electrically conductive thermal-memory filament that shrinks when heated to the extent that the cross-section of the overall skeleton becomes smaller. This feature facilitates extracting the endoprosthesis subsequent to treatment. Ideally the filament will respond to temperatures slight higher than the normal temperature of the blood. Such a characteristic will prevent damage to the tissue of the surrounding blood vessel or body cavity.

A slightly higher temperature is obtained in an embodiment by heat exchange from a slightly warmer liquid injected through the endoprosthesis from an auxiliary catheter upstream.

The endoprosthesis skeleton can be heated by passing an electric current through the insulated thermal-memory wire.

Only some of the endoprosthesis can be thrust out of the catheter into the blood vessel or body cavity. An endoprosthesis of this type usually expands automatically. The section inside the vessel or cavity is provided with separated skirts. The proximal skirt is overlapped by the endoprosthesis sleeve such that the sleeve tapers together where it extends into the catheter. The resulting conical section between the proximal skirt and the catheter is perforated. The perforations allow blood to flow almost unimpeded through both the vessel or cavity and the endoprosthesis.

The endoprosthesis in an advanced version of this embodiment can easily be positioned and displaced by a plunger that slides back and forth inside the catheter. The endoprosthesis can be extracted back out of the blood vessel or body cavity and through the catheter attached to the plunger.

Blood flow can be even further improved by mounting the catheter eccentric with respect to the expanded section of the endoprosthesis and providing the accordingly also eccentric conical sleeve section with at least one larger perforation. The accordingly improved blood flow will decrease the risk of thrombosis in the blood vessel or body cavity that is to be treated.

The filament in the endoprosthesis skeleton in one practical advanced version of this embodiment can be of highly elastic to superelastic metal, an alloy of nickel, tin, and aluminum for example. An endoprosthesis with this feature can be employed with a balloon-expanded skeleton.

Once an endoprosthesis has been implanted, in another embodiment, the space between it and the inner surface of the blood vessel or body cavity can be stuffed with a sponge, spongy gel, or other spongy material. The sponge can be saturated with a drug or other substance through the flexible tubing.

Metabolism will accordingly occur with the inner surface of the blood vessel or body cavity by way of the sponge. The endoprosthesis can be removed along with the stuffing once the vessel or cavity has been treated.

BRIEF DESCRIPTION OF THE DRAWINGS

Various embodiments of the present invention will now be specified with reference to the accompanying schematic drawing, wherein.

DESCRIPTION OF THE PREFERRED EMBODIMENTS

Figure 1:
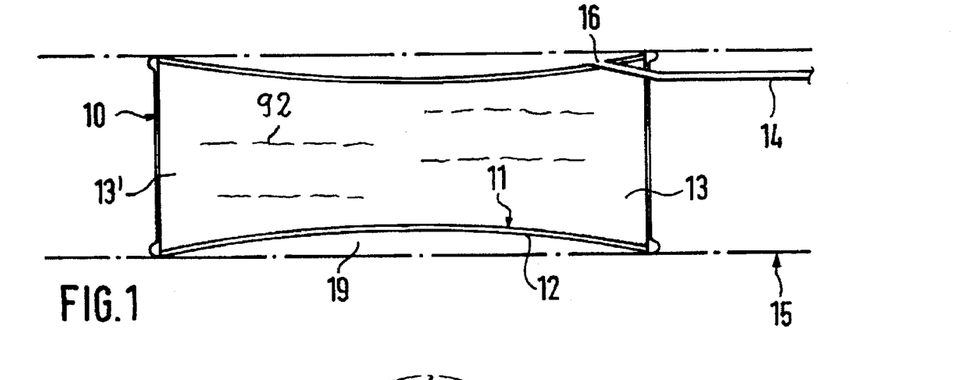
FIG. 1 is a longitudinal section through an implanted endoprosthesis in the form of an oblong cylinder with a skeleton in the form of a knit cylinder and with a sleeve around the skeleton with a skirt at each end resting tight against the inner surface of an incompletely indicated blood vessel or body cavity.

The endoprosthesis 10 represented implanted in FIG. 1 is an automatically expanding stent in the form of an oblong and hollow cylinder. It comprises a flexible tubular knit skeleton 11 snugly accommodated in a sleeve 12. Sleeve 12 is at least to some extent fastened to skeleton 11 and is made of a readily expanding elastic material. Communicating with the proximal end 13 of sleeve 12 is a length of flexible tubing 14. Flexible tubing 14 extends axially into endoprosthesis 10 through the lumen of the blood vessel 15. The tubing communicates with the vessel through a port 16 in the wall of the sleeve.

Figure 2:
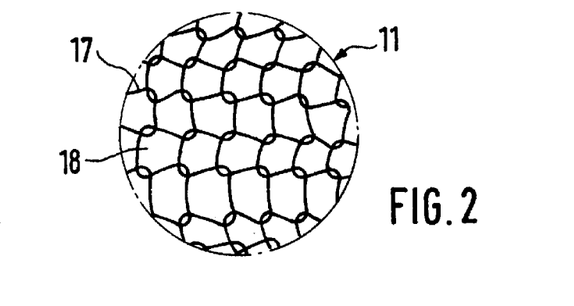
FIG. 2 is a detail illustrating how the skeleton has been knit of metal filament with open meshes.

FIG. 2 is a detail illustrating the fabric of the skeleton 11 that supports endoprosthesis 10. The fabric is a loose knit of metal filament 17 with open meshes 18. The particular advantages of a skeleton of this type are that endoprosthesis 10 will be flexible enough to follow the curvature of the blood vessel it is implanted in and will return once implanted subject to the inherent resilience of the skeleton to the state it was in prior to being compressed for implantation.

The skeleton 11 of the endoprosthesis 10 illustrated in FIG. 1 is narrow-waisted. Its ends 13 and 13' are accordingly wider than its midsection. This feature allows ends 13 and 13' to rest snug against the inner surface of the accommodating blood vessel 15 represented by the dot-and-dash lines in FIG. 1. Room 19 is accordingly left around sleeve 12 between it and the inner surface of the blood vessel. A drug can be injected into room 19 through flexible tubing 14 and allowed to penetrate gradually into the vessel's wall.

The flexible tubing 14 that communicates with blood vessel 15 through the port 16 in sleeve 12 in the vicinity of proximal end 13 can also be detachable from the sleeve. Such tubing can be extracted once the drug has been injected into room 19. It will be practical for port 16 to be provided with an unillustrated valve to close off the port while flexible tubing 14 is being extracted and prevent the drug in room 19 from leaking out.

Endoprosthesis 10 is implanted by a catheter while compressed. It is secured over the catheter with a wrapping that can be withdrawn toward proximal end 13. Once the catheter has been properly introduced into blood vessel 15, the wrapping that maintains it compressed is withdrawn and endoprosthesis 10 will expand subject to the inherent resilience of skeleton 11. The ends 13 and 13' of the narrow-waisted endoprosthesis 10 will come to rest snug against the inner surface of blood vessel 15.

Figure 3:
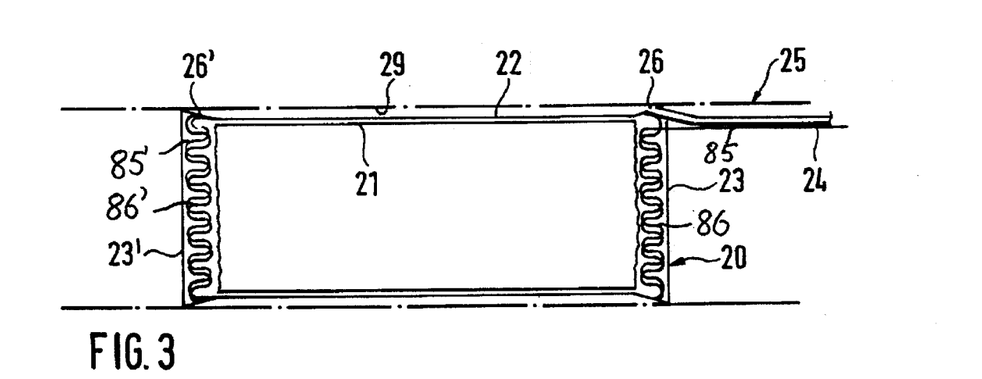
FIG. 3 is a section similar to that in FIG. 1 through another embodiment of the endoprosthesis with a skirt tapering radially out of each end of the sleeve.

Another type of endoprosthesis 20 is illustrated implanted in FIG. 3. It differs from the endoprosthesis 10 illustrated in FIG. 1 in that the sleeve 22 around skeleton 21 has a skirt 23 and 23' extending out of each end. Skirts 23 and 23' taper out and rest snug against the inner surface of the blood vessel 25. As in the embodiment illustrated in FIG. 1, a length of flexible tubing 24 extends through the lumen of the vessel and into the vicinity of proximal skirt 23 for the purpose of delivering a drug or other substance to room 29 left between the inner surface of the vessel and sleeve 22.

A substance that solidifies can also be injected instead of a drug into the annular room 29 between the inner surface of the blood vessel and the sleeve 22 around skeleton 21. Once the substance solidifies it will constitute a tunnel-like support for the blood vessel. Endoprosthesis 10 can be removed once the substance has solidified by pulling a drawstring that extends along with flexible tubing 24 out of the proximal end of skeleton 21, through the lumen of the blood vessel accommodating endoprosthesis 20, and out at the point of insertion. This drawstring is employed to open the meshes of skeleton 21. Once the meshes are open, sleeve 22 can easily be retracted from the site of implantation with flexible tubing 24. One end of the drawstring, however, can also be secured to the distal end 23' of sleeve 22, allowing the sleeve to be extracted by pulling the tube once the meshes have been opened.

Figure 4:
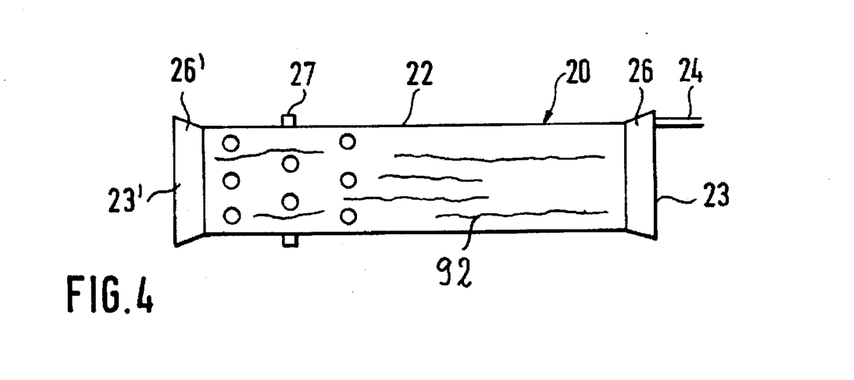
FIG. 4 illustrates the endoprosthesis illustrated in FIG. 3 unexpanded and with spacers projecting radially out of the midsection of the sleeve surrounding the skeleton.

When the room 29 between sleeve 22 and the inner surface of the blood vessel is stuffed with a solidifying substance, it has been demonstrated practical to provide the sleeve 22 that surrounds skeleton 21 with spacers 27 in the form of radially outward-projecting knobs as illustrated in FIG. 4. These spacers rest once the endoprosthesis has been implanted against the inner surface of the vessel.

The outside of sleeve 22 can also have corrugations instead of knobs. Once the substance injected into the room 29 between sleeve 22 and the inner surface of the blood vessel has solidified, the tunnel-like structure in such an endoprosthesis 20 will have a number of perforations or breaches to allow the flowing blood to nourish the wall of blood vessel 25.

It is practical for the sleeve 22 of an endoprosthesis 20 intended for the creation of a tunnel-like support for a blood vessel 25 by injecting a solidifying substance to be coated with an antiadhesive. The antiadhesive can for example be a thin layer of liquid silicone.

Figure 5:
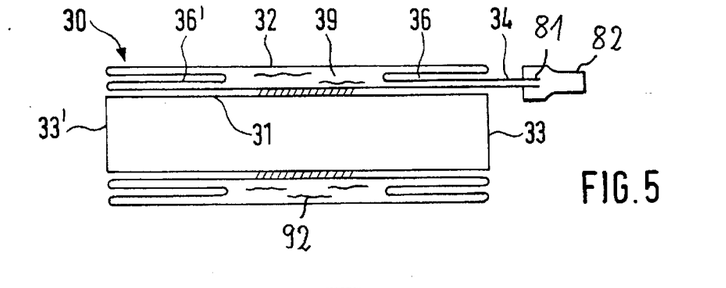
FIG. 5 is a longitudinal section through an endoprosthesis with a sleeve in the form of a hollow membrane surrounding the skeleton.

The endoprosthesis 30 illustrated in FIG. 5 comprises a sleeve 32 wrapped around a skeleton 31. The sleeve is a tubular knit in the form of a hollow membrane secured only to the midsection of skeleton 31. Sleeve 32, to which a length of flexible tubing 34 is also attached, is provided like a bellows with longitudinal folds 36 and 36' at the end. Flexible tubing 34 extends out of proximal end.

Figure 6:
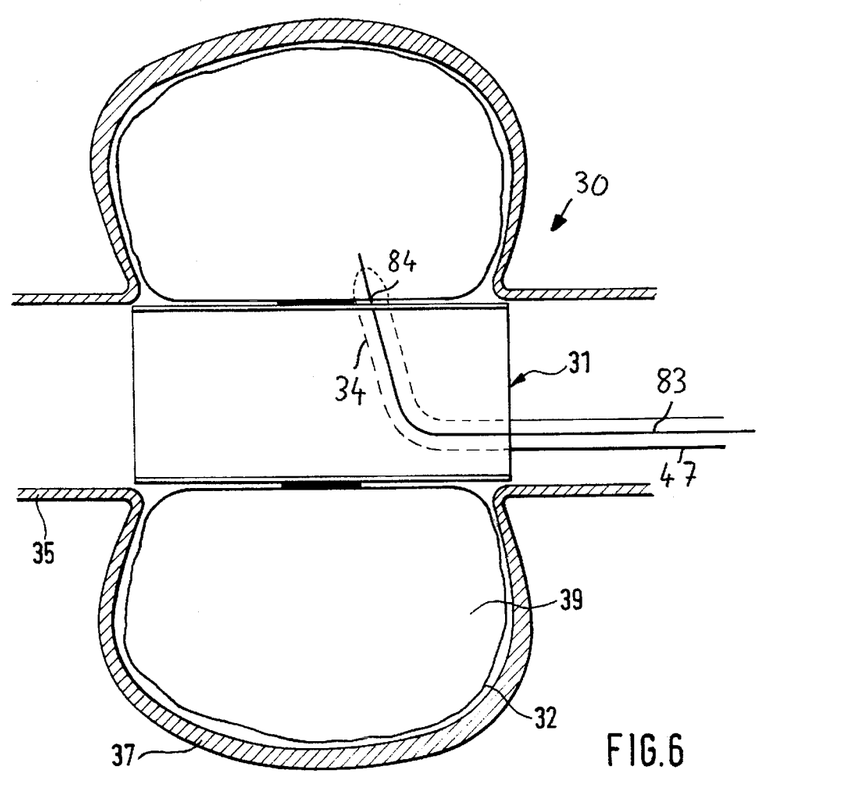
FIG. 6 is a longitudinal section similar to that in FIGS. 1 and 3 illustrating the endoprosthesis illustrated in FIG. 5 with its hollow membrane distended and occupying a bulge surrounding the blood vessel.

The endoprosthesis 30 illustrated in FIG. 5 is intended in particular for permanently packing aneurysms as illustrated in FIG. 6. Aneurysms are bulges in the wall of the blood vessel like the illustrated bulge 37, which can lead to severe hemorrhaging.

Such bulges 37 can be treated by introducing an endoprosthesis 30 with an unillustrated catheter into position in a blood vessel 35 as illustrated in FIG. 6. Once the endoprosthesis 30 is released, it will come to rest against the inner surface of the blood vessel. The sleeve 32 in the form of a hollow membrane is now stuffed with a solidifying substance through flexible tubing 34 and penetrates into the bulge 37 that surrounds the blood vessel, completely packing it. Once the substance has hardened, flexible tubing 34 is extracted and skeleton 31 removed if necessary by opening its meshes. The filaments of skeleton 31 are fastened, cemented for example, to sleeve 32 only at the midsection and will release when the meshes are opened.

Figure 7:
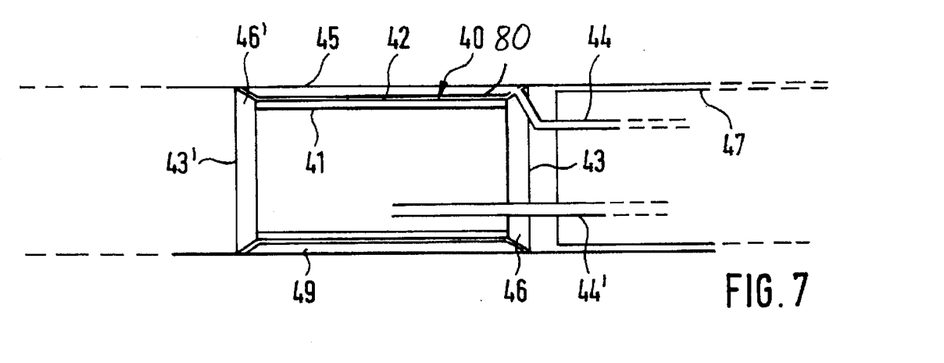
FIG. 7 is a longitudinal section through an implanted endoprosthesis with a main catheter and two auxiliary catheters.

The endoprosthesis 40 schematically illustrated in FIG. 7 is implanted in a blood vessel 45 with a main catheter 47 and with its skeleton 41 surrounded by a sleeve 42. There are skirts 46 and 46' around the ends 43 and 43' of the endoprosthesis sealing off the room 49 between the sleeve and the inner surface of the vessel. Sleeve 42 is attached to one auxiliary catheter 44 and skeleton 41 to another auxiliary catheter 44'. Endoprosthesis 40 can be extracted subsequent to treatment of blood vessel 45 by pulling second drawstring 44'. The resulting traction on skeleton 41 decreases its cross-section, and the skeleton can be extracted from the blood vessel by a pull on main catheter 47. The sleeve collapses and can be extracted from the vessel by a pull on first auxiliary catheter 42.

Figure 8:
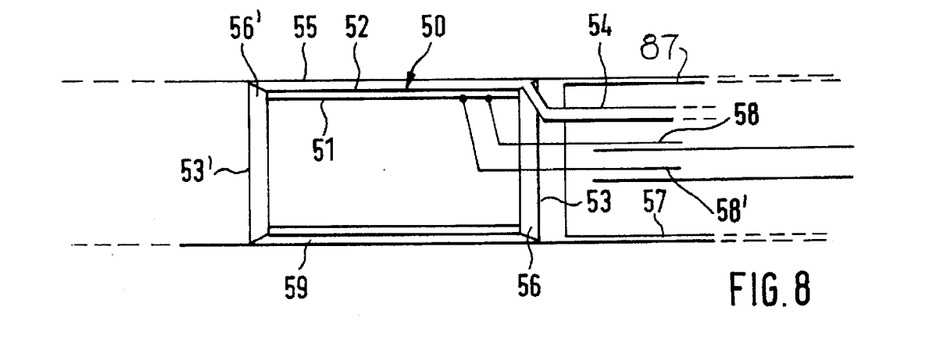
FIG. 8 is a longitudinal section through an implanted endoprosthesis with a skeleton of electrically conductive thermal-memory filament.

The endoprosthesis 50 schematically illustrated in FIG. 8 is implanted in a blood vessel 55 with a main catheter 57 and with its skeleton 51 surrounded by a sleeve 52. There are skirts 56 and 56' around the ends 53 and 53' of the endoprosthesis sealing off the room 59 between the sleeve and the inner surface of the vessel. Skeleton 51 is knit out of electrically conductive thermal-memory filament. Skeleton 51 is connected to an incoming-current line 58 and an outgoing-current line 58' such that as much as possible of the fabric of skeleton 51 can be electrified. Current lines 58 and 58' extend mutually insulated along the flexible tube 54 in main catheter 57. Endoprosthesis 50 can to advantage be extracted while current is flowing through skeleton 51, raising the skeleton's temperature slightly above the normal temperature of the blood. The surrounding tissue will not be affected by the slightly higher temperature. The heat will, however, contract the thermal-memory filament, and the more slender skeleton can be extracted through main catheter 57.

Figure 9:
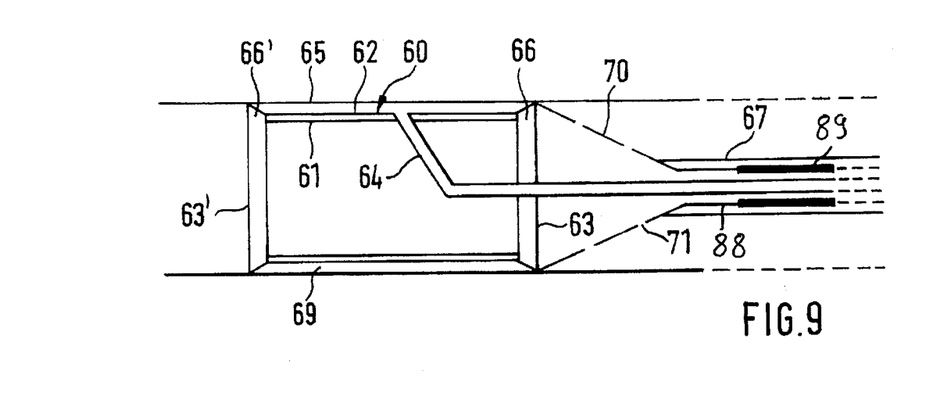
FIG. 9 is a longitudinal section through an implanted endoprosthesis incompletely displaced out of a main catheter.

The endoprosthesis 60 illustrated in FIG. 9 is implanted in a blood vessel 65 with a main catheter 67 and with its skeleton 61 surrounded by a sleeve 62. There are skirts 66 and 66' around the ends 63 and 63' of the endoprosthesis sealing off the room 69 between the sleeve and the inner surface of the vessel. Endoprosthesis 60, however, does not extend all the way into blood vessel 65. One section is forced out of main catheter 67 and into the blood vessel by an unillustrated plunger, and the other section remains inside. The section accommodated in the vessel expands automatically. Sleeve 62 overlaps the proximal end 63 of skirt 66 and then tapers together inside main catheter 67. The conical section 70 of sleeve 62 is provided with large perforations 71 that allow the blood to flow almost unimpeded through the blood vessel 65 being treated. The risk of thrombosis is accordingly considerably reduced. If main catheter 67 is eccentric in relation to endoprosthesis 60, conical section 70 will be somewhat larger and will be able to accommodate somewhat larger perforations 71. Blood perfusion will accordingly not be affected to the same extent.

Blood vessels can be similarly treated with narrow-waisted balloon catheters instead of endoprostheses in accordance with the present invention. Such a catheter must be provided with flexible tubing for delivering drugs or other substances. Blood flow through the vessel being treated with such a catheter will, however, be interrupted during the treatment.

Thus, the sleeve may be more voluminous than the skeleton and is initially wrapped around it, leaving wrinkles 92, as shown in FIGS. 1, 4 and 5.

The outside of the sleeve may be coated with an antiadhesive 80 as shown in FIG. 7.

The flexible tubing may be releasable from the sleeve which has a port 81, shown in FIG. 5, at the point of communication. The endoprosthesis, furthermore, is provided with means 82 for closing the port upon removal of the tubing, as shown also in FIG. 5.

The sleeve 32 shown in FIG. 6, may be punctured by an angiography lead 83 applied by the catheter 47 (FIG. 6). At least one length of the flexible tubing 34 extends along the lead 83 and into the endoprosthesis 30, and enters the sleeve through a puncture 84 produced by the lead 83.

A drawstring 85 shown in FIG. 3 extends out of the proximal end of the skeleton, and is employed to open up the meshes 86 in the fabric.

The distal end of the sleeve is attached to a drawstring 85' on the skeleton, as shown in FIG. 3. The sleeve can be comprised of biodegradable material.

An auxiliary catheter 87, shown in FIG. 8, may infuse fluid heated slightly warmer than the temperature of circulating blood through a port immediately upstream of the proximal end of the skeleton.

The implanted endoprosthesis has an expandable section 70 and a non-expanding section 88, as shown in FIG. 9.

Figure 9A:
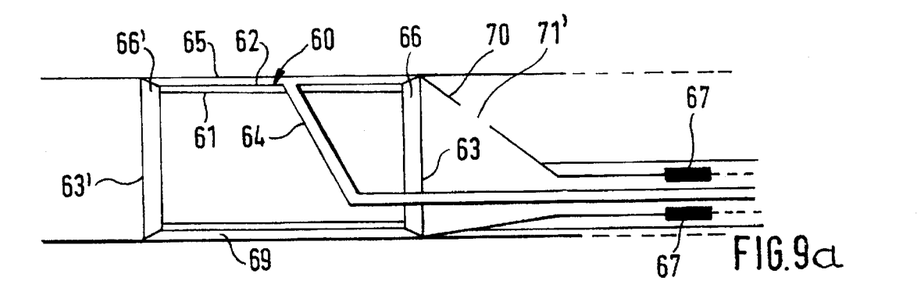
FIG. 9a is a longitudinal section through an implanted endoprosthesis showing a main catheter with an eccentrically arranged conical section.

A plunger 87, as shown in FIG. 8, travels back and forth inside the main catheter 67. This main catheter 67, furthermore, may be eccentric relative to the expanded section of the endoprosthesis, and is a larger proximal-end conical section 70 of the sleeve 62 which is provided with a wider perforation 71, as shown in FIG. 9a.

A balloon catheter 90 may be inside the main catheter 67 connected to the endoprosthesis 60 and intended to expand the section of the endoprosthesis that is to be implanted in the blood vessel.

Figure 9B:
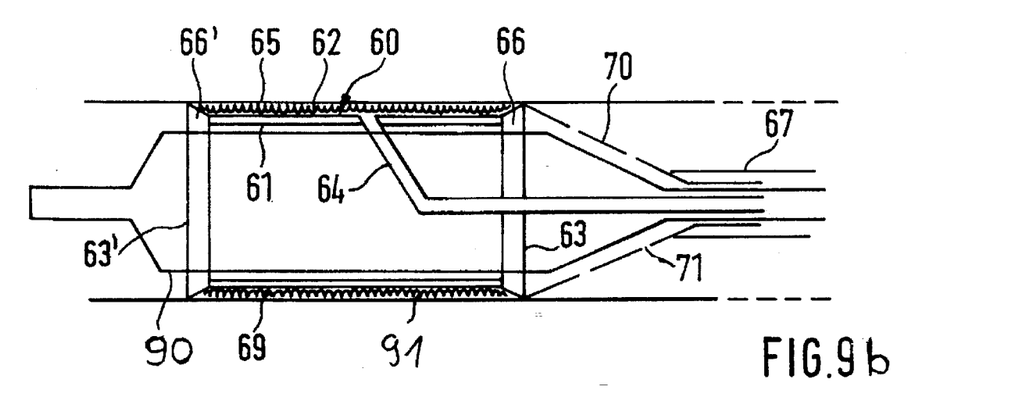
FIG. 9b is a longitudinal section through an implanted endoprosthesis showing a sleeve being wrapped in a gel or liquid-impregnated sponge.

The sleeve, furthermore, may be wrapped in gel or liquid-impregnated sponge 91, as shown in FIG. 9b.

I claim:

1. An endoprosthesis that can be percutaneously implanted by a catheter in a patient's body inside a blood vessel or other body cavity, comprising:

a sleeve and a skeleton with an outside, said sleeve surrounding at least the outside of said skeleton, said endoprosthesis being oblong and hollow and being expandable when implanted to fit a lumen of the vessel or cavity;

said sleeve and said skeleton being initially narrow enough to be implanted and being expandable once they have been implanted;

said sleeve and said skeleton being configured such that when implanted, a space is left between the outer surface of said sleeve of the implanted endoprosthesis and an inner surface of the vessel or cavity said endoprosthesis is implanted in; and at least one length of flexible tubing extend through said sleeve for delivering medication to said space.

2. An endoprosthesis as defined in claim 1, wherein said sleeve is comprised of a plasticly deformable material with a specific elasticity.

3. An endoprosthesis as defined in claim 1, wherein said sleeve is comprised of an elastic material with a specific elasticity.

4. An endoprosthesis as defined in claim 1, wherein said sleeve has a volume sleeve greater than said skeleton and is initially wrapped around said skeleton leaving wrinkles.

5. An endoprosthesis as defined in claim 1, wherein said skeleton has a midsection and ends, said midsection being narrower than said ends once the endoprosthesis has been implanted and expanded.

6. An endoprosthesis as defined in claim 1, wherein said sleeve has ends with skirts tapering radially out.

7. An endoprosthesis as defined in claim 6, wherein said skirts are resilient and seal said space tight.

8. An endoprosthesis as defined in claim 6, wherein said skirts are broadened radially out.

9. An endoprosthesis as defined in claim 5, wherein said sleeve has spacers projecting radially out between said ends of said skeleton.

10. An endoprosthesis as defined in claim 5, including a first auxiliary catheter communicating with said sleeve adjacent a proximal end of said skeleton; and a second auxiliary catheter with said skeleton adjacent said space.

11. An endoprosthesis as defined in claim 1, wherein said sleeve has an outside coated with an antiadhesive.

12. An endoprosthesis as defined in claim 1, wherein said sleeve comprises a hollow tubular membrane, space being left between said sleeve and said skeleton at a midsection of the endoprosthesis.

13. An endoprosthesis as defined in claim 12, wherein said sleeve has a volume greater than said skeleton, is at least partially attached to said skeleton, and is initially wrapped around said skeleton, leaving wrinkles.

14. An endoprosthesis as defined in claim 1, wherein said sleeve is folded in longitudinally from each of said ends of said skeleton.

15. An endoprosthesis as defined in claim 1, wherein said flexible tubing is releasable from said sleeve, said sleeve having a port at a point of communication with said flexible tubing; and means for closing said port upon removal of said tubing.

16. An endoprosthesis as defined in claim 15, wherein said sleeve is a self-repairing membrane that can be punctured by an angiography lead applied by the catheter, at least one length of said flexible tubing extending along said lead and into said endoprosthesis and entering said sleeve through a puncture produced by said lead.

17. An endoprosthesis as defined in claim 15, wherein said sleeve can be punctured by an angiography lead applied by the catheter, at least one length of said flexible tubing extending along said lead and into said endoprosthesis and entering said sleeve through a puncture produced by said lead, said puncture being sealable upon extraction of said tubing by a polymerizable substance delivered through said tubing.

18. An endoprosthesis as defined in claim 1, wherein said sleeve is comprised of biodegradable material.

19. An endoprosthesis as defined in claim 1, wherein said skeleton is comprised of a fabric with meshes.

20. An endoprosthesis as defined in claim 19, including a drawstring extending out of a proximal one of said ends for opening said meshes in said fabric.

21. An endoprosthesis as defined in claim 20, wherein said drawstring is fastened to said flexible tubing and extends out of said proximal one of said ends of said skeleton.

22. An endoprosthesis as defined in claim 20, wherein a distal end of said sleeve is attached to a drawstring on said skeleton.

23. An endoprosthesis as defined in claim 5, wherein the fabric is obtained from an insulated electrically conductive thermal-memory filament.

24. An endoprosthesis as defined in claim 1, including an auxiliary catheter for infusing fluid heated slightly warmer than the temperature of circulating blood through a port immediately upstream of a proximal end of said skeleton of said endoprosthesis.

25. An endoprosthesis as defined in claim 24, including an incoming-current line and an outgoing-current line extending along said flexible tubing and electrically connected to said skeleton.

26. An endoprosthesis as defined in claim 1, including a main catheter, said endoprosthesis when implanted having an expandable section and a non-expanding section and being attached to said main catheter so that said expandable section extends into a blood vessel and said non-expanding section remains inside said main catheter; a proximal radially-outward tapering skirt on said expanded section overlapping said sleeve, said sleeve merging proximally into said main catheter through a conical section with perforations in the form of meshes.

27. An endoprosthesis as defined in claim 26, including a plunger traveling back and forth inside said main catheter and being attachable to a section of the endoprosthesis remaining inside said main catheter.

28. An endoprosthesis as defined in claim 26, wherein said main catheter is eccentric relative to said expanded section of the endoprosthesis and comprising a large proximal-end conical section of said sleeve, said conical section having a wide perforation.

29. An endoprosthesis as defined in claim 26, wherein said skeleton is comprised of highly elastic to super elastic filament.

30. An endoprosthesis as defined in claim 26, including a balloon catheter inside said main catheter connected to the endoprosthesis and expanding the section of the endoprosthesis to be implanted in said blood vessel.

31. An endoprosthesis as defined in claim 1, wherein said sleeve is wrapped in a liquid-impregnated sponge expanding to completely occupy said space when the endoprosthesis has been implanted, at least one said flexible tubing communicating with said space.

* * * * *